(12) United States Patent
Goncalves

(10) Patent No.: US 11,202,516 B2
(45) Date of Patent: Dec. 21, 2021

(54) THERAPEUTIC ORTHOPEDIC MATTRESS

(71) Applicant: Vanderlei Goncalves, Orlando, FL (US)

(72) Inventor: Vanderlei Goncalves, Orlando, FL (US)

(*) Notice: Subject to any disclaimer, the term of this patent is extended or adjusted under 35 U.S.C. 154(b) by 272 days.

(21) Appl. No.: 15/853,340

(22) Filed: Dec. 22, 2017

(65) Prior Publication Data
US 2018/0116421 A1 May 3, 2018

Related U.S. Application Data

(63) Continuation of application No. 15/622,332, filed on Jun. 14, 2017, now abandoned.

(60) Provisional application No. 62/334,535, filed on May 11, 2016.

(51) Int. Cl.
| | | |
|---|---|---|
| A47C 27/08 | (2006.01) | |
| A47C 27/15 | (2006.01) | |
| A61N 2/00 | (2006.01) | |
| A47C 27/14 | (2006.01) | |
| A61N 2/06 | (2006.01) | |
| A47C 31/00 | (2006.01) | |
| A61G 7/057 | (2006.01) | |
| A47C 27/12 | (2006.01) | |
| A61N 5/06 | (2006.01) | |

(52) U.S. Cl.
CPC .......... *A47C 27/088* (2013.01); *A47C 27/146* (2013.01); *A47C 27/15* (2013.01); *A47C 31/004* (2013.01); *A61N 2/00* (2013.01); *A61N 2/008* (2013.01); *A61N 2/06* (2013.01); A47C 27/125 (2013.01); A61G 7/05715 (2013.01); A61G 7/05784 (2016.11); A61N 2005/0659 (2013.01)

(58) Field of Classification Search
CPC ... A47C 27/088; A47C 31/004; A47C 27/146; A47C 27/15; A47C 27/125; A47C 21/006; A47C 21/003; A61N 2/06; A61N 2/008; A61N 2/00; A61N 2005/0659; A61G 7/05784; A61G 7/05715; A61H 2201/0146; A61H 2201/10
USPC .......................................................... 5/727
See application file for complete search history.

(56) References Cited

U.S. PATENT DOCUMENTS

| | | | | |
|---|---|---|---|---|
| 3,953,687 A | * | 4/1976 | Carbonneau | H04R 9/025 335/222 |
| 4,143,435 A | * | 3/1979 | Masuda | A47C 31/003 5/693 |
| 4,509,219 A | * | 4/1985 | Yagi | A47C 21/00 5/693 |
| 5,138,730 A | * | 8/1992 | Masuda | A47C 27/146 5/693 |

(Continued)

FOREIGN PATENT DOCUMENTS

CN 10290212 B * 9/2012 ............ A47C 27/00

*Primary Examiner* — Nicholas F Polito
*Assistant Examiner* — Luke Hall
(74) *Attorney, Agent, or Firm* — Matthew G. McKinney, Esq.; Allen, Dyer et al.

(57) ABSTRACT

A mattress made of natural latex foam has at least four layers. Each of the layers having a density that is different than the density of the adjacent layers. The mattress may also have on the first layer a plurality of magnets and infrared elements. The mattress may also have massage elements and/or a low frequency energy element between the second and third layers.

14 Claims, 5 Drawing Sheets

(56) References Cited

U.S. PATENT DOCUMENTS

| | | | | |
|---|---|---|---|---|
| 6,088,858 | A * | 7/2000 | Juster | A47C 21/022 |
| | | | | 5/496 |
| 6,616,595 | B2 * | 9/2003 | Riach, Jr. | A61N 2/00 |
| | | | | 335/209 |
| 6,702,730 | B2 * | 3/2004 | Bonile | A61N 2/008 |
| | | | | 5/693 |
| 7,546,653 | B2 * | 6/2009 | Ye | A47C 21/044 |
| | | | | 5/421 |
| 8,758,216 | B2 * | 6/2014 | Anderson | A61N 2/02 |
| | | | | 600/14 |
| 2005/0182287 | A1 * | 8/2005 | Becker | A61N 2/02 |
| | | | | 600/13 |
| 2008/0093784 | A1 * | 4/2008 | Rawls-Meehan | A47C 27/148 |
| | | | | 267/80 |
| 2009/0320209 | A1 * | 12/2009 | McCain | A47C 31/006 |
| | | | | 5/636 |
| 2010/0229302 | A1 * | 9/2010 | De Bock | A47C 27/122 |
| | | | | 5/248 |
| 2011/0256369 | A1 * | 10/2011 | Switzer | A47C 27/144 |
| | | | | 428/215 |
| 2014/0324132 | A1 * | 10/2014 | Wey | A61N 5/06 |
| | | | | 607/88 |
| 2017/0119169 | A1 * | 5/2017 | Krim | A47C 21/046 |

* cited by examiner

THERAPEUTIC ORTHOPEDIC MATTRESS

REFERENCE TO RELATED CASE

This application is a continuation-in-part of application Ser. No. 15/622,322 filed Jun. 14, 2017, now abandoned, which claims priority to Provisional Application Ser. No. 62/334,535 filed May 11, 2016, the contents of which are hereby incorporated by reference in their entirety.

FIELD OF THE INVENTION

People spend about a third of their time lying on a mattress. While the person may be asleep most of the time, if the mattress does not provide the correct support, then the person may be awake for at least a portion of the time. Many times the lack of support causes lower back pain or numbness in extremities. With the incorrect materials, the person may end up lying in a hole created by the weight of the person being in the same position on the mattress over a long period of time. Such a situation does not provide for the rest and relaxation needed for the body to repair itself over night. Thus, there is a need for a mattress that provides the correct support, is made of natural materials that resist mold, mildew and bugs. Also provided are a number of therapies that can be used in conjunction with the mattress to further assist in allowing a body to recover from the stresses and strains of that day.

SUMMARY OF THE INVENTION

The present invention is directed to a mattress having a plurality of layers that includes first layer having a first density, the first layer having a plurality of valleys and peaks, a second layer having a second density, a third layer having a third density, and a fourth layer having a fourth density, wherein each layer has a different density than an adjacent layer.

In some embodiments, the first layer has one of magnets and infrared elements disposed thereon.

In some other embodiments, the second layer has one of massage elements and a low frequency energy element disposed thereon.

According to another aspect of the present invention, there is provided a mattress having a plurality of layers that includes a first layer having a first density, the first layer having a plurality of valleys and peaks, a second layer having a second density, a third layer having a third density, and a fourth layer having a fourth density, wherein each layer has a different density than an adjacent layer and at least two layers have a therapeutic element disposed thereon.

It is to be understood that both the foregoing general description and the following detailed description of the present embodiments of the invention are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and, together with the description, serve to explain the principles and operations of the invention.

DETAILED DESCRIPTION OF THE PREFERRED EMBODIMENTS

Figure 1:
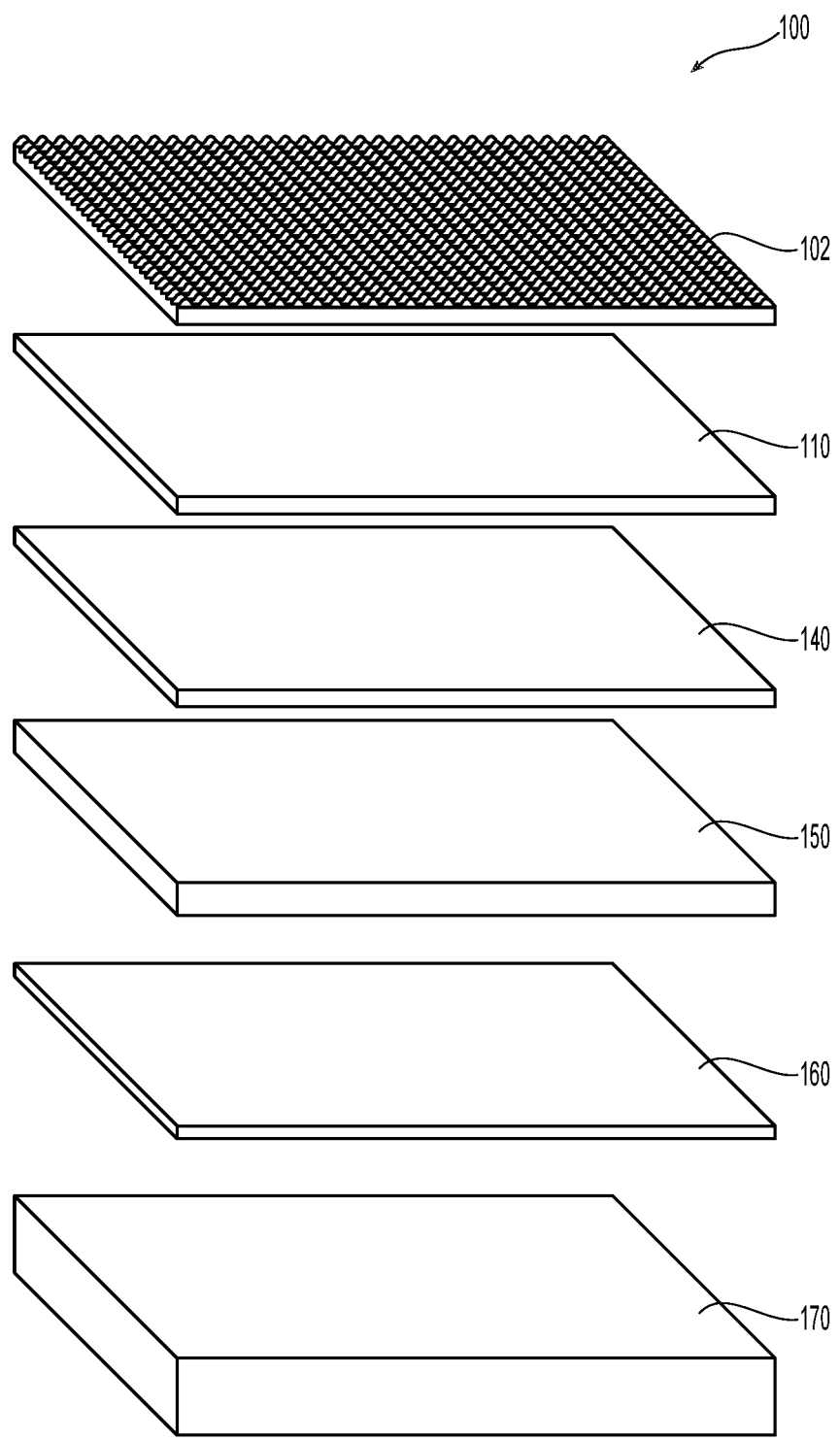
FIG. 1 represents an exploded perspective view of one embodiment of a mattress according to the present invention.

Reference will now be made in detail to the present preferred embodiment(s) of the invention, examples of which are illustrated in the accompanying drawings. Whenever possible, the same reference numerals will be used throughout the drawings to refer to the same or like parts.

Referring to FIG. 1, there is one embodiment of a mattress 100 according to the present invention. The mattress 100 has a number of layers. A first layer 102 is made of all Natural Latex Foam in convoluted design (Egg Crate style). The first layer 102 can be made with foam of different densities (soft, medium or firm), and the thickness of the foam may vary from one inch up to three inches depend on the height of the mattress that is required by the user.

The convoluted (egg crate) design is essentially a system of bubbles interlinked or a peak-and-valley structure that allows the user a feeling of muscle relaxation through the corporal's movements during the night, proportioning a self-massage "do-in-type" with a total relaxation. The touch points (peaks) make the user feel as if hundreds of fingers are massaging the user's body.

The peak-and-valley structure allows greater air circulation between the mattress and the user, facilitating evaporation of perspiration to keep the body cool, benefiting the skin to breathe more oxygen and reducing heat buildup, allowing the airflow to move heat away as the user sleeps, creating a clean environment. The peak-and-valley structure can also improve blood flow by decreasing pressure on the skin, especially at pressure points such as hips and shoulders.

On the surface of the first layer 102, in the valleys, are inserted all near/far infrared buttons or discs 104 and/or magnetic buttons or discs 106. The magnetic buttons or discs 106 are inserted with North pole (Negative pole) facing the users—or upward and away from the other layers of the mattress.

The near/far infrared buttons or discs 104 are rounded discs of measuring about ¼ inch thick by ½ inch in diameter. They are made of micro-sized particles composition having excellent properties of at least 99% of purity, and contain titanium oxide, platinum, aluminum oxide and silver compound infused into a ceramic powder. The near/far infrared buttons or discs 104 are capable of emitting far infrared rays at high efficiency, and have excellent durability and transparency. The near/far infrared rays are safe energy, effective, and extremely beneficial for all living beings on earth; it is the natural form of energy, called vital energy. Far Infrared wave produces vibratory movements molecular that is capable to activate over 60 trillion of cells in our body, breaking up the water molecules (clusters), generating a process of spalling of the molecules, helping the expulsion of free radicals and toxins of the organism, assisting in detoxification and alkalization of the cells, increasing the body immunity, maintaining a healthy body, which may prevent diseases. The far infrared rays also cause dilation of blood vessels and speeds up blood circulation, expands capillaries which stimulates regeneration and oxygenation, allowing healthy cells to perform their normal functions. The far infrared rays relieve pain and is a method to prevent a thrombosis.

The magnetic buttons or discs 106 are preferably ceramic ferrite magnetic buttons or discs. The discs 106 have a manufacturers gauss rating of 3650-3950 and a surface output of 1500-2000 Gauss They are rounded discs that are preferably ¼ inch-thick×½ inch in diameter. The magnetic field may be effective in relieving minor pain, helping to improve blood circulation, re-energizing the body, restoring the immune system with ability of natural self-repair, and preventing illness and promote deep restorative sleep along with an amazing therapeutic experience.

Figure 2:
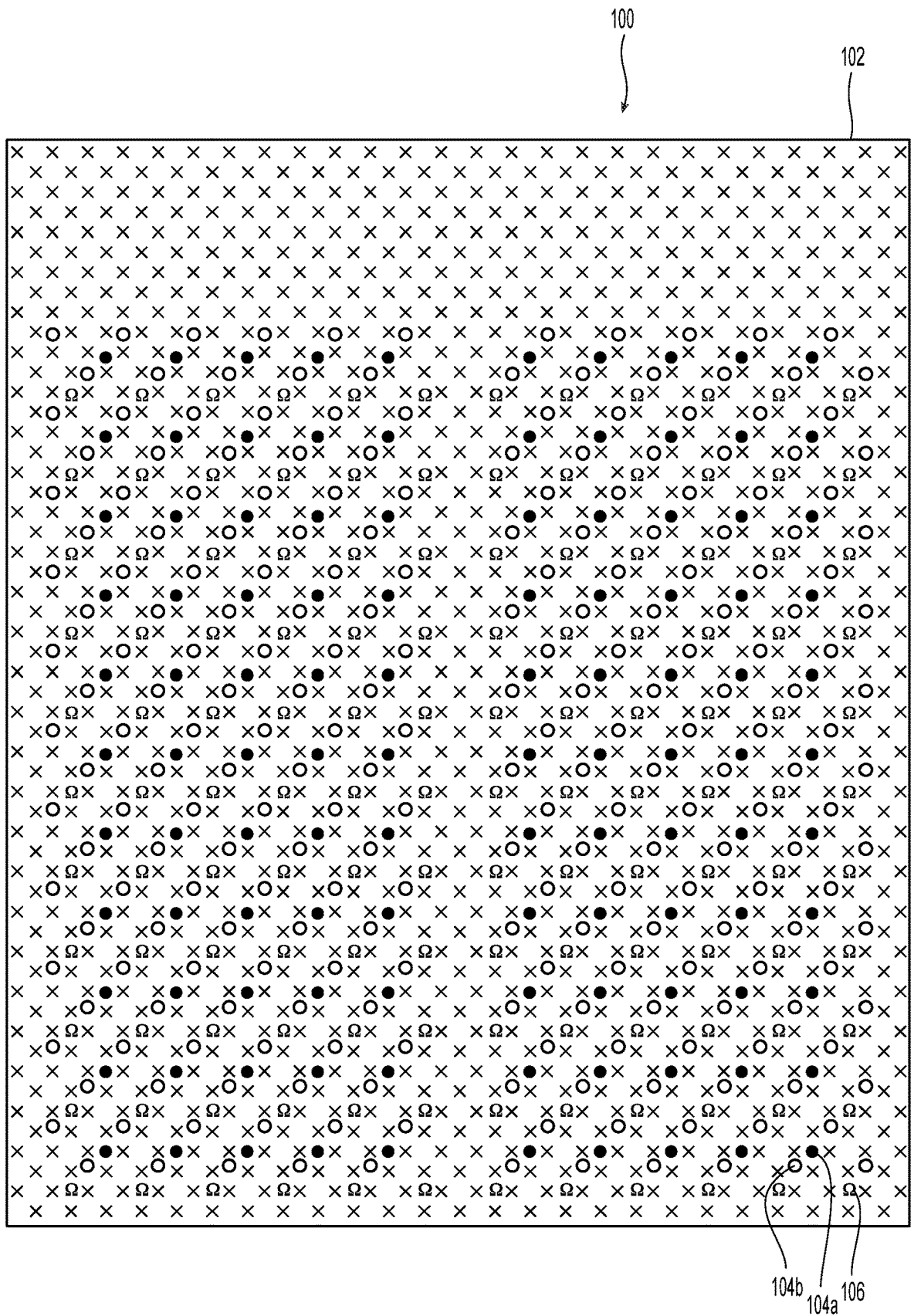
FIG. 2 is a representation of a top view of a first layer of the mattress of FIG. 1 showing the locations of magnets and infrared elements.

As illustrated in FIG. 2, there is the first layer 102 and the peaks of the peak-and-valley structure are illustrated with an "x" in the figure. There may be more or fewer of the peaks and valleys, depending on the user's wants or needs. As illustrated in FIG. 2, the magnetic buttons or discs 106 are represented by an Ω and are disposed between the peaks "x" and in the valleys. Also illustrated in FIG. 2 are the near infrared buttons 104a with a ● and the far infrared buttons 104b with a °.

As illustrated in FIG. 2, the magnetic buttons or discs 106 and the infrared buttons 104 are preferably not in the region where the user's head would be (at the top of the figure in FIG. 2). As but one example, the distance from the head of the mattress to the first of the magnetic buttons or discs 106 and the infrared buttons 104 would be about 20 inches. The distance between the head of the mattress to the first of the magnetic buttons or discs 106 and the infrared buttons 104 could be less or greater depending on the user's specific needs or requirements.

Also within the scope of the present invention is that the number and location of the magnetic buttons or discs 106 and the infrared buttons 104 can be varied. For example, the magnetic buttons or discs 106 may be the only elements disposed on the first layer 102 and they may be only at the foot of the bed or only in the middle of the mattress 100.

The same may be done with the infrared buttons 104; the infrared buttons 104 may be the only elements disposed on the first layer 102 or with the magnetic buttons or discs 106. They may also only be at the foot of the bed or only in the middle of the mattress 100. There may only be far infrared buttons 104b, only near infrared buttons 104a, or both.

The first layer 102 has a mattress cover on top thereof (not illustrated) and is attached (glued) with water based glue to the second layer 110. The second layer 110 is made of all Natural Latex Foam of different densities (soft, medium or firm), and the thickness of the foam may vary from one inch up to four inches depending on the height of the mattress required by the user.

Figure 3:
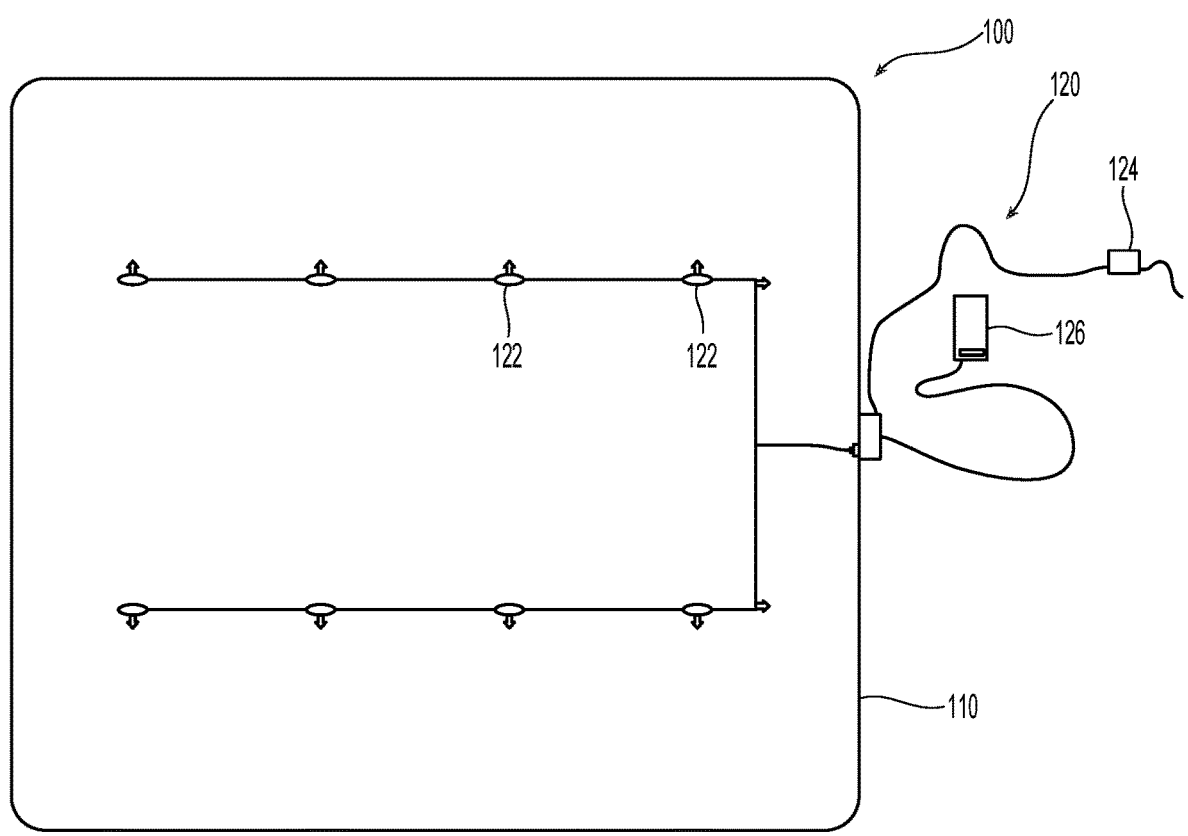
FIG. 3 is a top view of a second layer of the mattress of FIG. 1 with massage elements disposed thereon.

The second layer 110 preferably has a vibration massager 120 that can be installed in between the first layer 102 and the second layer 110. The vibration massager 120 has a plurality of vibrator motors 122 enclosed in a safe plastic capsules that are attached to the top of the second layer 110. The vibration massager 120 has a power supply 124 to supply power the to the motors and a control module 126 to control the plurality of vibrator motors 122. The control module 126 can control the duration, frequency, and strength of the vibrations supplied by the plurality of vibrator motors 122. The user may also be able to chose that the vibrator motors on one side of the mattress be activated at any given time. The number of vibrator motors 122 is preferably 8 for the larger mattresses: Full, Queen, King, and California King. For the smaller mattresses, it has been found that 4 of vibrator motors 122 are sufficient to provide massage to the user. However, it is understood that the number, spacing, and location of the vibrator motors 122 can be different from those illustrated in FIG. 3.

The vibration massager 120 produces a micro-vibration massage that provides an improvement in stress relief and helps in the expansion of the pores to promote a deep relaxation of muscles for better quality of life. It has been determined that the vibration massager 120 may also be used for temporary relief of minor muscle, back and joint pain, may increase local circulation and relaxation of muscles where applied. It will also assist in removing dead cells from the skin surface, increasing the brightness and elasticity of the skin.

Figure 4:
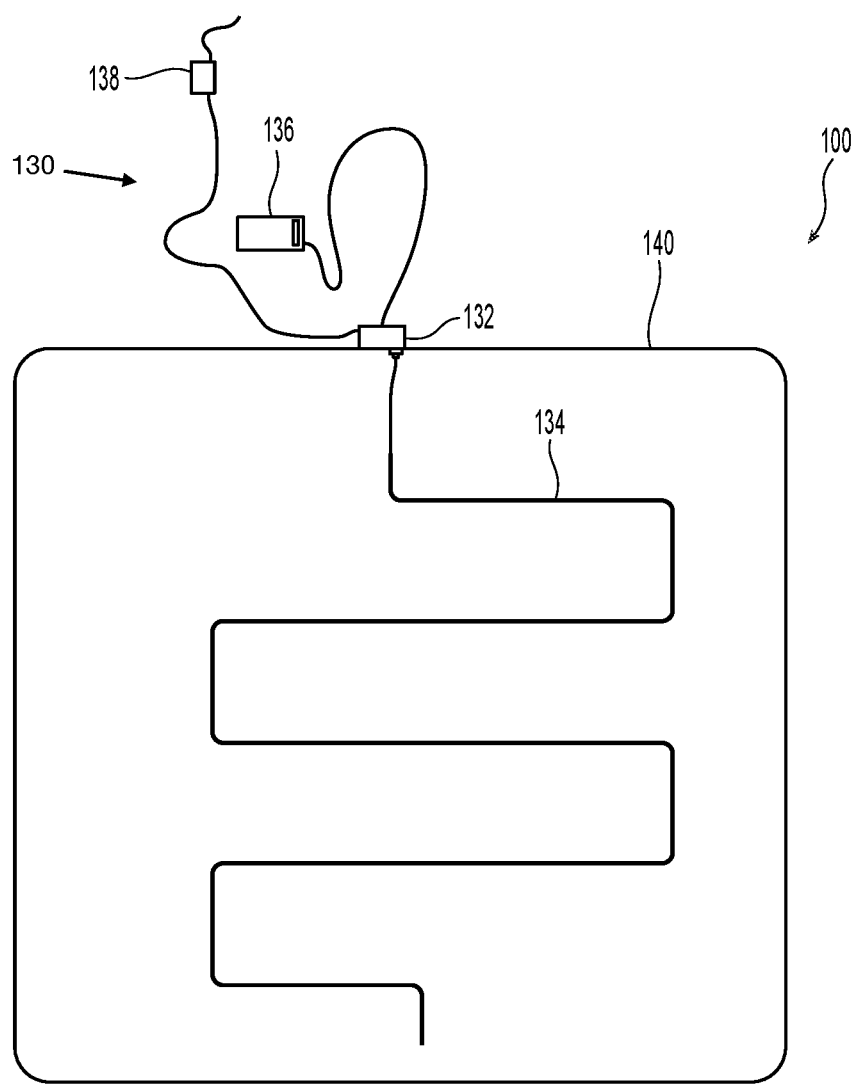
FIG. 4 is a top view of a second layer of the mattress of FIG. 1 with a low frequency energy element disposed thereon.

Another system that may also be included on the second layer 110 is a low-frequency pulsed electro-magnetic field (PEMF) system 130, which recharges the cells of the body. As illustrated in FIG. 4. a PEMF (Pulsed Electro-Magnetic Field) system 130 is an electrical system represented by a microprocessor 132 with an antenna 134 that is internally installed in the mattress in between the first and the second layer. The system 130 also includes a controller 136 and a power supply 138. The low frequency signal is amplified by the microprocessor and then distributed throughout the antenna 134 to the entire surface of the mattress 100. The pulsed electromagnetic field is an extremely low frequency signal that varies in a range of 5 Hz to 86 Hz. The cycle may be repeated while the system remains ON. The system 130 emits pulsed low frequency of electro-magnetic waves through the antenna from the generator, generating a sequence of low frequency of pulsed electro-magnetic field starting at 7.83 Hz, then increasing by 2 Hz from 10 to 50 Hz, each of the pulse's durations is 5 seconds. Once the frequency reaches 52 Hz to 60 Hz, the time between frequencies jump to 30 seconds. Between 62-82 Hz, the intervals return to 5 seconds. The system 130 can then be programmed to automatically start again with the same process. The pulsed electromagnetic waves with different frequencies and intensities reaches the acupuncture points to induce restoring energy, relax the nerves, reduces stress and encourages relaxation to sleep. The PEMF system 130 provides the temporary relief by re-energizing cells, forcing them to work in the appropriate frequency; recharges body's cells, allowing them to float freely; contributes to activate cell metabolism processes; stimulates cell renewal and regeneration; helps the body to mobilize its forces from self-treatment; helps to absorb nutrients and remove toxins from the body; relieving minor muscle and joint pain and assisting in the relaxation of muscles; reducing stress and encouraging relaxation improving good sleep; improves circulation; and reduces pain.

Figure 5:
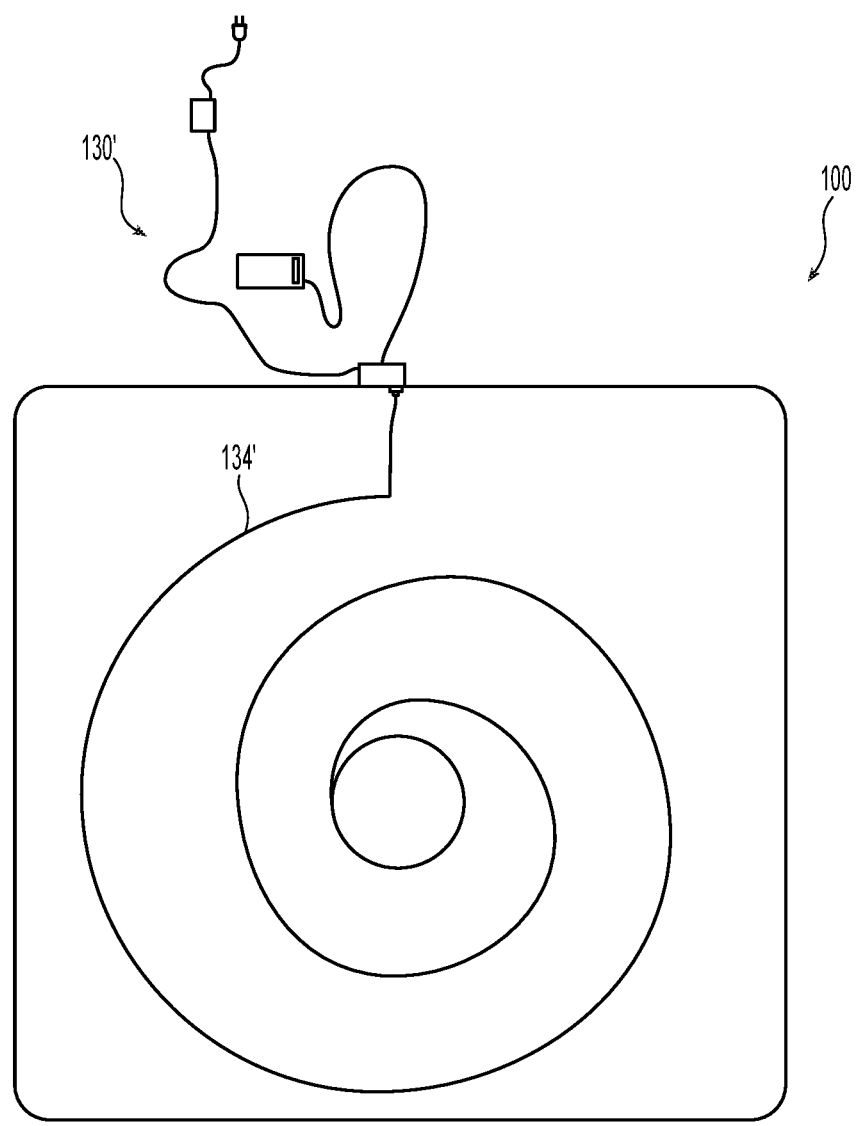
FIG. 5 is a top view of a second layer of the mattress of FIG. 1 with a different low frequency energy element disposed thereon.

FIG. 5 illustrates a second PEMF system 130' that is similar to that in FIG. 4 but has a different configuration for the antenna 134'.

The third layer 140 it is made of all Natural Latex Foam of different densities (soft, medium or firm), and the thickness of the foam may vary from one inch up to four inches depending on the height of the mattress that is wanted by the user. The purpose of this third layer 140 is to give stability, thereby providing an orthopedic support for more durability, resulting in a uniform and firm product to absorb motion and reduce wear to the mattress.

The vibration massager 120 may also be disposed between the second 110 and the third 140 layers of the mattress. The same is also possible with the PEMF systems.

The fourth layer 150 is made of all Natural Latex Foam of different densities (soft, medium or firm), and the thickness of the foam may vary from one inch up to four inches depend on the height of the mattress needed by the user.

The fifth layer 160 is made of an insulator pad or other materials with hard (extra firm) surface and the thickness may vary from ⅛ inches up to one inch. This fifth layer adds strength, long durability and support, giving stability to prevent the mattress from sagging where the personsleep.

The sixth layer 170 is a support box (orthopedic box support). It is made of very firm (high density) polyurethane foam, or can be made with selected wooden box covered (incased) with foam. It was designed to provide an orthopedic support for the other layers. The thickness of the box may vary from two inches up to ten inches depend on the height of the mattress.

It should be noted that each of the layers are independent layers that are then attached to the adjacent layer(s) with a water-based glue. In one embodiment, there are at least four layers and the density of each layer is different from an adjacent layer. Thus, the second layer has a different density that the first and third layers. Similarly, the third layer has a density that is different than the second and fourth layers. For example, one embodiment has the first and third layers as being firmer (higher density) than the second and fourth layers.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

I claim:

1. A mattress comprising:
   a first natural latex foam layer having a first density, the first layer having a plurality of valleys and peaks;
   a second natural latex foam layer having a second density;
   a third natural latex foam layer having a third density;
   a fourth natural latex foam layer having a fourth density;
   an antennae comprising an elongated wire having a first end positioned proximate a first end of the mattress and a second end longitudinally spaced apart from the first end proximate a second opposing end of the mattress, the antennae spread out between the first and second natural latex foam layers; and
   a microprocessor coupled to the first end of the antennae and configured to distribute a plurality of sequences of intermittent electrical signals along the antennae to the second end;
   wherein each natural latex foam layer has a different density than an adjacent layer.

2. The mattress according to claim 1, further comprising a fifth layer, the fifth layer being a rigid layer and thinner than each of the first, second, third and fourth natural latex foam layers.

3. The mattress according to claim 1, wherein the first natural latex foam layer has one of magnets and infrared elements disposed thereon.

4. The mattress according to claim 1, wherein the second natural latex foam layer includes massage elements disposed thereon.

5. The mattress according to claim 1, wherein the first natural latex foam layer includes magnets and infrared elements disposed thereon.

6. The mattress according to claim 3, wherein the magnets each comprise a positive pole surface and an opposing negative pole surface and the magnets are disposed in a plurality of valleys of the first natural latex foam layer with the positive pole side adjacent to the first natural latex foam layer.

7. The mattress according to claim 1, wherein a layout of the antenna includes a plurality or bends from the first end to the second end.

8. The mattress according to claim 1, wherein the first natural latex foam layer includes magnets and infrared elements disposed thereon and the second natural latex foam layer includes massage elements.

9. The mattress according to claim 8, wherein the mattress has a head portion, a foot portion and a middle portion, the magnets, infrared elements, massage elements, and the antennae being disposed on portions of the mattress other than the head portion.

10. A mattress comprising:
    a first layer having a first density, the first layer having a plurality of valleys and peaks;
    a second layer having a second density;
    an antennae comprising an elongated wire having a first end positioned proximate a first end of the mattress and a second end longitudinally spaced apart from the first end towards a second end of the mattress; and
    a microprocessor coupled to the first end of the antennae and configured to distribute a plurality of sequences of intermittent electrical signals along the antennae to the second end.

11. The mattress according to claim 10, wherein additional therapeutic elements are selected from the group of therapeutic elements consisting of magnets, infrared elements, and massage elements to be positioned on the first or second layers.

12. The mattress according to claim 11, wherein the magnets are ceramic ferrite magnets disposed on the first layer.

13. The mattress according to claim 10, wherein each sequence of intermittent electrical signals is configured to increase in frequency.

14. The mattress according to claim 10, wherein the antennae has a plurality of bends as the antennae extends from the first end to the second end.

* * * * *